United States Patent
Voute et al.

(10) Patent No.: US 7,228,688 B2
(45) Date of Patent: Jun. 12, 2007

(54) SCALED DOWN FREEZING AND THAWING SYSTEM FOR BIOPHARMACEUTICALS AND BIOLOGICS

(75) Inventors: Nicolas Voute, Cuges les Pins (FR); Richard Wisniewski, Mateo, CA (US); Eric K. Lee, Acton, MA (US); Jonathan N. Webb, Zionsville, IN (US)

(73) Assignee: Integrated Biosystems, Inc., Napa, CA (US)

(*) Notice: Subject to any disclaimer, the term of this patent is extended or adjusted under 35 U.S.C. 154(b) by 401 days.

(21) Appl. No.: 10/735,378

(22) Filed: Dec. 12, 2003

(65) Prior Publication Data

US 2004/0139753 A1    Jul. 22, 2004

Related U.S. Application Data

(60) Provisional application No. 60/433,357, filed on Dec. 13, 2002.

(51) Int. Cl.
*F25D 25/00* (2006.01)
*F25D 23/12* (2006.01)
*F25D 11/00* (2006.01)

(52) U.S. Cl. .............................. 62/62; 62/337; 62/440
(58) Field of Classification Search .................. 62/62, 62/337, 440
See application file for complete search history.

(56) References Cited

U.S. PATENT DOCUMENTS

| | | | |
|---|---|---|---|
| 1,528,890 A * | 3/1925 | Petersen ................... 220/23.2 |
| 3,586,097 A * | 6/1971 | Bender et al. ............... 392/444 |
| 3,952,536 A | 4/1976 | Faust et al. .................... 62/293 |
| 4,117,881 A * | 10/1978 | Williams et al. .............. 435/1.3 |
| 4,251,995 A | 2/1981 | Pert et al. ........................ 62/60 |
| 4,453,385 A | 6/1984 | May ................................. 62/3 |
| 4,565,073 A * | 1/1986 | Lavender ...................... 62/373 |
| 4,799,358 A | 1/1989 | Knopf et al. ..................... 62/3 |
| 4,852,358 A | 8/1989 | Acharya et al. ................ 62/63 |
| 5,022,236 A | 6/1991 | Knippscheer et al. ......... 62/529 |
| 5,205,128 A | 4/1993 | Richard .......................... 62/63 |
| 5,255,520 A | 10/1993 | O'Geary et al. .............. 62/3.2 |
| 5,582,028 A * | 12/1996 | Rilling et al. ................. 62/530 |
| 5,863,715 A | 1/1999 | Rajotte et al. ............... 435/1.3 |
| 6,065,294 A | 5/2000 | Hammerstedt et al. ........ 62/3.3 |
| 6,196,296 B1 | 3/2001 | Wisniewski et al. .......... 165/47 |
| 6,347,525 B2 | 2/2002 | Cosman ......................... 62/65 |
| 6,393,860 B1 * | 5/2002 | Heschel et al. ............... 62/376 |
| 2002/0020516 A1 | 2/2002 | Wisniewski et al. .......... 165/61 |

FOREIGN PATENT DOCUMENTS

| EP | 1 134 000 A2 | 9/2001 |
|---|---|---|
| WO | WO 98/23907 | 6/1998 |
| WO | WO 98/34078 | 8/1998 |
| WO | WO 01/50852 A2 | 7/2001 |
| WO | WO 03/006899 A1 | 1/2003 |
| WO | WO 03/037082 A1 | 5/2003 |

* cited by examiner

*Primary Examiner*—William C. Doerrler
(74) *Attorney, Agent, or Firm*—Wayne F. Reinke, Esq.; Heslin Rothenberg Farley & Mesiti P.C.

(57) ABSTRACT

A freezing and thawing unit for small amounts of biopharmaceuticals and biologics. The freezing and thawing unit is reduced in scale, as compared to a corresponding commercial or large-scale process. The freezing and thawing unit can be used for testing, preservation and/or processing of small quantities of biopharmaceuticals and biologics.

47 Claims, 7 Drawing Sheets

SCALED DOWN FREEZING AND THAWING SYSTEM FOR BIOPHARMACEUTICALS AND BIOLOGICS

CROSS-REFERENCE TO PRIOR APPLICATION

Priority is claimed to U.S. Provisional Application Ser. No. 60/433,357, filed on Dec. 13, 2002, which is herein incorporated by reference in its entirety.

BACKGROUND OF THE INVENTION

1. Technical Field

The present invention generally relates to the freezing and thawing of biopharmaceuticals and biologics. More particularly, the present invention relates to the preservation and processing by controlled freezing and thawing of small amounts or samples of biopharmaceuticals and biologics, using a reduced-scale system.

2. Background Information

Preservation (storage by freezing) and processing (freezing and thawing) of biopharmaceuticals and biologics (collectively, "bioproducts"), for example, including, but not limited to proteins, cells, antibodies, medicines, plasma, blood, biological buffer solutions, cell culture media, viruses, serum, cell fragments, cellular components, and any other bioproduct, is often required on a large scale using adapted commercial-sized freezing equipment with a subsequent thawing in a room. These methods produce suboptimal process conditions leading to significant product degradation or loss. For example, bioproducts can be frozen and thawed in containers ranging from 1 to 500 liters.

However, companies and research institutions engaging in the freezing and thawing of bioproducts in such large volumes do so largely without the ability to fully test how the bioproducts will react in the process using the intended equipment. This adds risk and cost, particularly if the bioproducts are damaged in the process.

Even an established routine for preservation and processing of labile bioproducts in small amounts, carried out using small containers such as vials or bottles, and placed in laboratory freezers with a constant temperature setpoint, or in special freezing chambers that can provide changing temperature profiles of the chamber environment, carries risk. Such freezing methods suffer from temperature gradients from container to container, leading to significant differences in the freezing and processing conditions, and subsequent product degradation or/and loss. Further, preservation and processing by placing the small container into a cold nitrogen gas (typically generated from a liquefied nitrogen), cooling them over a certain period of time and then plunging them into the liquid nitrogen may deliver differences in cooling and freezing from container to container as well as uncontrolled freezing across the product volume.

In addition, thawing of small amounts of bioproducts is typically accomplished by leaving them in a room environment, thus leading to slow and uncontrolled thawing which may be detrimental to the product. Rapid and controlled thawing may produce higher quality and minimize or eliminate product degradation and/or loss.

The preservation and processing by freezing and thawing of small amounts of bioproducts is typically associated with supercooling of product prior to freezing. The supercooling of product in small containers depends on the container size, temperature gradients, cooling rate and the presence of ice nucleation sites. The supercooling may differ from container to container, leading to an unrepeatable process. The supercooling is followed by a rapid (flash) freezing of a part of product volume with the temperature rise to about 0° C. and a subsequent slower freezing of the remaining part of the product. Both supercooling and flash freezing can be detrimental to the product, and, since they occur in an unrepeatable way, the product quality may vary among the containers. Minimization or elimination of supercooling can provide uniform product processing and higher overall product quality.

Thus, a need exists for a way to reliably and repeatedly conduct the freezing (without supercooling) and thawing processing for small quantities of bioproducts in a controlled way all across the product volume, thereby providing consistent freezing and thawing conditions.

SUMMARY OF THE INVENTION

Briefly, the present invention satisfies the above-noted need by providing apparatus, system and method for freezing and/or thawing of small amounts of a bioproduct.

In accordance with the above, it is an object of the present invention to provide a freezing and thawing unit for freezing and/or thawing of small amounts of a bioproduct.

The present invention provides, in a first aspect, apparatus for freezing and/or thawing at least one bioproduct. The apparatus comprises a unit for freezing and/or thawing at least one bioproduct on a small scale, the unit comprising at least two opposite surfaces. At least one of the opposite surfaces is coupleable to at least one driving device for freezing and/or thawing. At least one of (a) a proportional spacing of the opposite surfaces, and (b) a first dimension of a bioproduct container for the unit, corresponds to a second dimension of a bioproduct container for a larger-scale unit. The first dimension and second dimension are different dimensions.

The present invention provides, in a second aspect, a system for performing freezing and/or thawing of at least one bioproduct on a small scale. The system comprises a unit for freezing and/or thawing at least one bioproduct on a small scale, the unit comprising at least two opposite surfaces, at least one driving device for freezing and/or thawing coupleable to at least one of the opposite surfaces, and at least one container for containing at least one bioproduct specimen within the unit. At least one of (a) a proportional spacing of the opposite surfaces, and (b) a first dimension of the at least one container, corresponds to a second dimension of a bioproduct container for a larger-scale unit. The first dimension and the second dimension are different dimensions.

The present invention provides, in a third aspect, a method of performing freezing and/or thawing of at least one bioproduct on a small scale. The method comprises providing a unit for freezing and/or thawing at least one bioproduct, the unit comprising at least two opposite surfaces. The method further comprises coupling at least one of the opposite surfaces to at least one driving device for freezing and/or thawing, and performing freezing and/or thawing on the at least one bioproduct, wherein the bioproduct is situated within the unit. At least one of (a) a proportional spacing of the opposite surfaces, and (b) a first dimension of a bioproduct container for the unit corresponds to a second dimension of a bioproduct container for a larger-scale unit. The first dimension and second dimension are different dimensions.

These, and other objects, features and advantages of this invention will become apparent from the following detailed description of the various aspects of the invention taken in conjunction with the accompanying drawings.

DETAILED DESCRIPTION OF THE INVENTION

Figure 1:
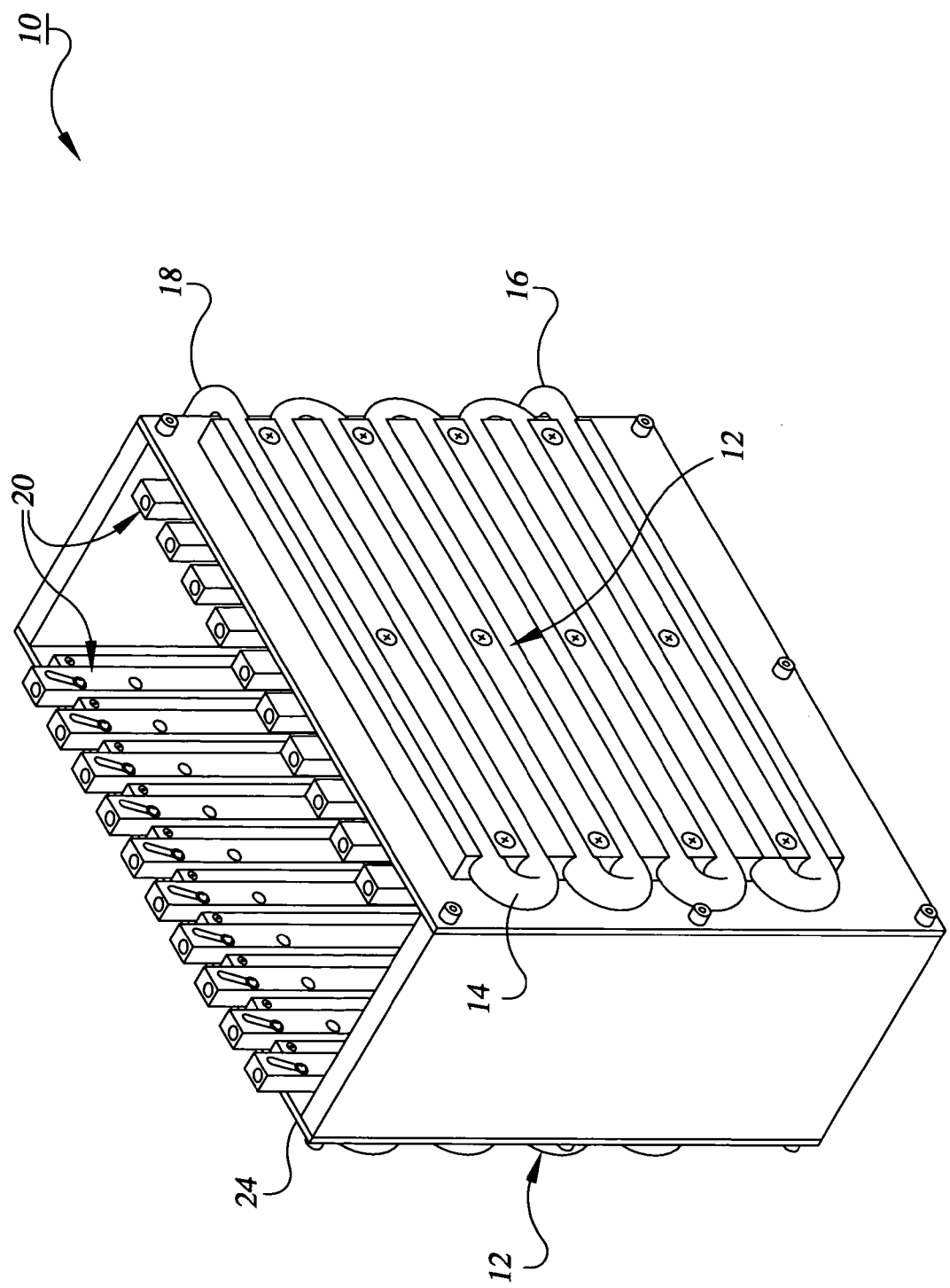
FIG. 1 depicts one example of a freezing and thawing unit with freezing/thawing driving devices in accordance with the present invention.

FIG. 1 depicts one example of a freezing and thawing unit 10 with freezing/thawing driving devices 12 coupled thereto, in accordance with the present invention. In the present example, the freezing/thawing driving devices are identical, though they need not be. The freezing and thawing unit in the present example is rectangular in shape, though other shapes are possible, such as, for example, prismatic trapezoidal, rhomboidal, cylindrical, or oval. The side panels of the unit (e.g., side panel 24) can be made of various materials, such as, for example, metal. The side panels can be coupled together in a variety of ways, for example, by bolting them together. One example of a metal is stainless steel. Preferably, the material of the side panel is chosen to compliment the intended application. For example, if a slow freezing or thawing process is desired, a polymer material is an example, and if a moderate freezing or thawing process is desired, stainless steel is one example of a material that will help achieve that goal.

Although two freezing/thawing driving devices are present in unit 10 in FIG. 1, it will be understood that a different number, for example, one freezing/thawing driving device coupled to one side, could be used.

Unit 10 can be used, for example, to test the freezing and thawing characteristics on a sample size of a bioproduct. As another example, unit 10 can be used for independent preservation and processing of small quantities of bioproducts, where the container size(s) used (see FIG. 3) is essentially the final product volume.

As shown, the freezing/thawing driving devices in FIG. 1 are coupled to opposite sides of the freezing and thawing unit in order to create a straight freezing path for the bioproducts. Freezing/thawing driving devices 12 each comprise a winding conduit 14 through which a heat-transfer fluid (not shown) would flow, for example, from an input 16 to an output 18 of the conduit. The freezing/thawing driving devices can take the form of, for example, plates with conduits for a heat-exchange medium, such as, for example, heat exchange fluid. The freezing/thawing driving device inner channels for fluid flow are designed to provide flow uniformity and turbulization for controlled and uniform heat transfer flux from the unit/container to the fluid during freezing and from the fluid into the unit/container during thawing. Examples of the types of heat-transfer fluid that could be used include liquid silicone, ethylene glycol and salt-based brine. One way to monitor and control the freezing process is to monitor the temperature of the coolant at both the input and the output. The monitoring could be automated (e.g., using computers and/or controllers), and the temperature of the heat-transfer fluid at the input controlled to effect the degree/speed or pattern of freezing required for the particular application. For example, the coolant temperature could be controlled to duplicate the freezing pattern of the bioproduct in a larger container.

In another embodiment, the single, winding conduit 14 shown in FIG. 1 could instead be a number of discrete conduits in parallel horizontally, with the flow in each conduit running either in the same direction or opposite directions for immediately adjacent conduits. Such a design addresses the issue of a temperature gradient between the side panel (e.g., side panel 24) top and bottom.

The contact between the heat-conducting structures (e.g., freezing/thawing driving devices 12 in FIG. 1) and the sides of the freezing and thawing unit (e.g., side panel 24 in FIG. 1), and the heat-conducting structures and the heat-transfer medium (e.g., heat-transfer fluid) determines the freezing and thawing initialization and the subsequent movement of the liquid-solid interfaces. The example designs herein demonstrate a high uniformity of heat flux between the product/container and the heat conducting structures and the heat-transfer medium. The example designs ensure high heat flux uniformity through those components, and therefore assures consistency of freezing and thawing.

Figure 2:
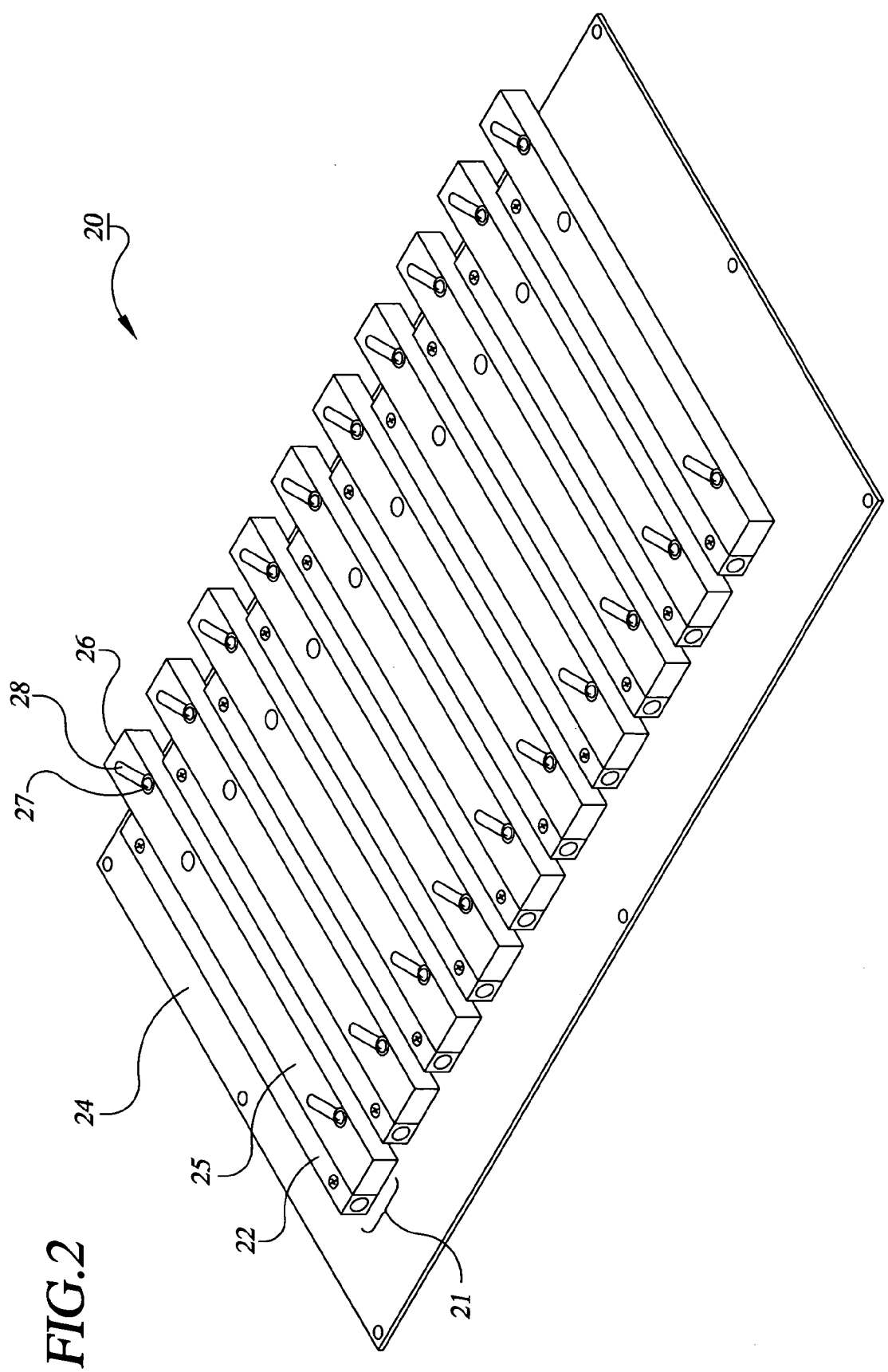
FIG. 2 depicts one side of the freezing and thawing unit of FIG. 1 to show details of the clamping system.
Figure 3:
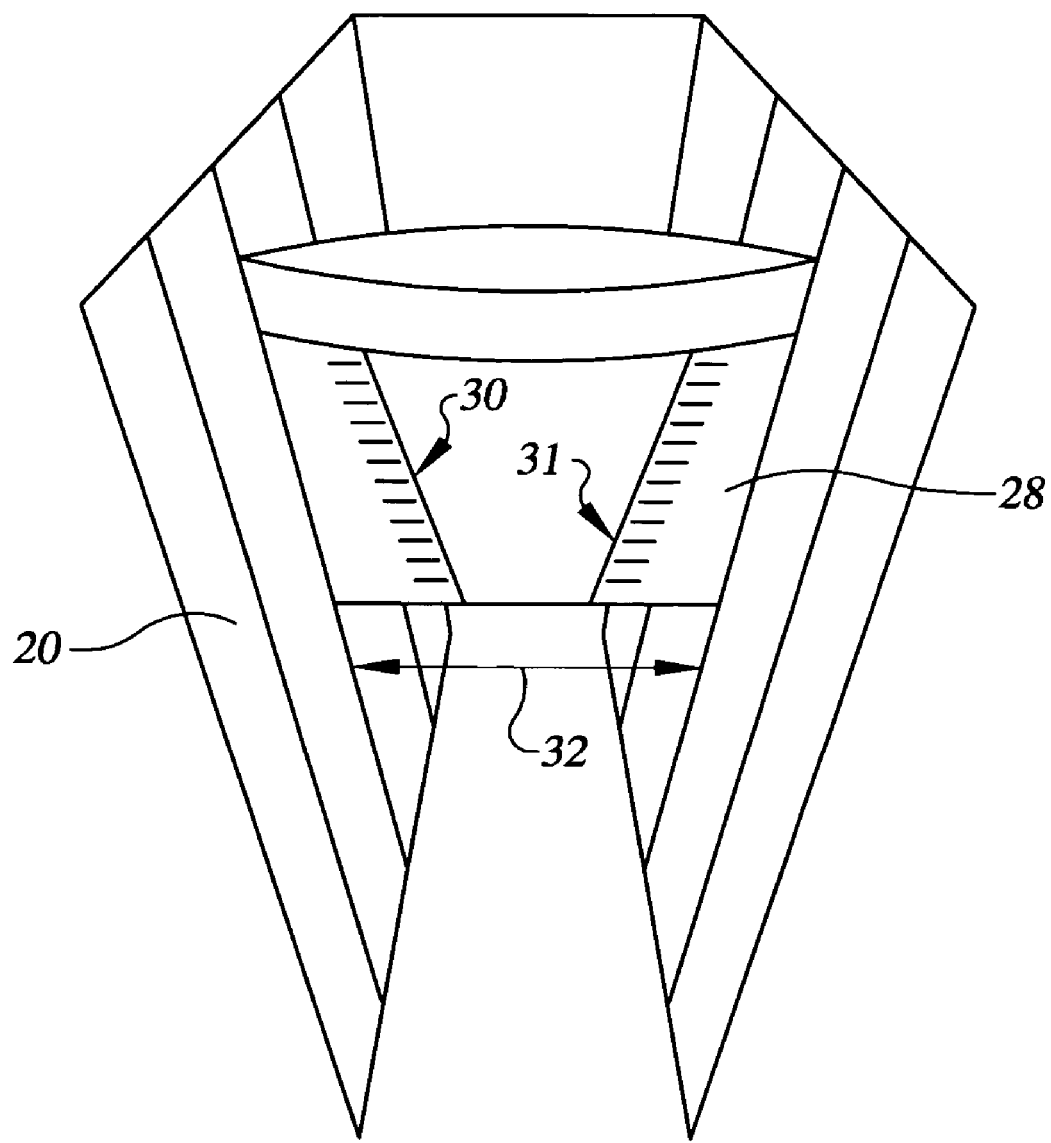
FIG. 3 depicts a specimen sample bag in a partially frozen state in the freezing and thawing unit of FIG. 1.

Freezing and thawing unit 10 also comprises two clamping arrays 20, best shown in FIG. 2. In the present example, the clamping arrays are identical, however, it will be understood that they need not be. As shown in FIG. 3, the purpose of the clamping arrays 20 is to hold multiple containers (bag 28 in this example) storing the bioproducts for processing and preservation. As such, various mechanical designs could accomplish this goal without departing from the spirit of the present invention; the present clamping arrays are merely one example of a mechanism to accomplish that goal. As shown, the placement of the freezing/thawing driving devices results in freezing fronts 30 and 31 moving inward toward the center of the bag. The freezing fronts form a tapered shape with the bottom of the bag freezing earlier than the top, thus allowing the unfrozen liquid to expand vertically as the freezing portion of the product undergoes volumetric mass expansion due to the liquid-solid transition. The taper angle can encompass a large range from a slight negative angle (about minus 15 degrees) through zero degrees and positive, as shown, less than 90 degrees.

Also shown in FIG. 3, a useable width 32 of unit 10 is preferably made to correspond to the distance between the freezing surfaces that are used in the corresponding large-scale process when used for testing, in order to maximize the information obtained regarding freezing of the bioproduct. For example, a useable width of 8 cm between opposite sides is common in large-scale containers for bioproducts which contact cooled or heated surfaces on each side for freezing or thawing, respectively. However, it will be understood that a variety of widths could be applied to mimic the larger-scale process, as well as freezing/thawing the bioproducts, for example, some proportion of the width in the larger-scale process. Consequently, when used for testing purposes, the unit is preferably sized to provide information that could be extrapolated to indicate what would be experienced at a larger scale, for example, by keeping the same aspect ratio.

Useable width 32 of unit 10 corresponds to a useable width for bag 28. In another example, the useable width of bag 28 approximates a thickness for a larger-scale bag in order to simulate a cross-section or "slice" of the larger-scale bag. This correspondence maximizes the information obtainable from processing of the small-scale bag that is useful for purposes of extrapolating to indicate an expected experience at the larger-scale. In the present example, if a larger bag is desired in the small-scale process, in order to maintain this correspondence with the larger-scale bags, the size of the smaller-scale bags are preferably changed only in height.

Returning now to FIG. 2, each clamping array comprises an array of clamping pairs, e.g., clamping pair 21. Each pair comprises a first element 22 that is stationary with respect to panel 24 and a second element 25 that is moveable with respect to panel 24. Element 25 is spring loaded in the clamping position shown. For example, one or more springs may be situated within element 25 and coupled to the fastener holding element 25 to panel 24 (i.e., connector 27). In such an example, the spring would push element 25 in one direction and the slots would shift element 25 towards first element 22, into a closed position. When an operator pushes down on end 26 of element 25, element 25 moves downward and away from element 22, due to movement of connector 27 along angled slot 28. In this manner, the clamping arrays allow easy bag insertion and removal.

The clamps and freezing/thawing driving devices in the present example are situated in relation to the bioproduct containers to provide the necessary localized temperature gradients and nucleation sites to ensure minimization or elimination of liquid supercooling. The shape of the freezing/thawing driving devices in contact with the sides of the freezing and thawing unit provide heat conduction patterns, as well as the local temperature gradient, beneficial to early ice nucleation in the container ends. The freezing/thawing driving devices can be profiled to produce optimum heat conduction pattern and the temperature profile for ice nucleation and subsequent heat removal (and delivery for thawing) between the unit and the freezing/thawing driving devices. The freezing/thawing driving devices can be, for example, solid, or hollow with, for example, a heat-transfer fluid circulated through them, as in FIG. 1.

Figure 4:
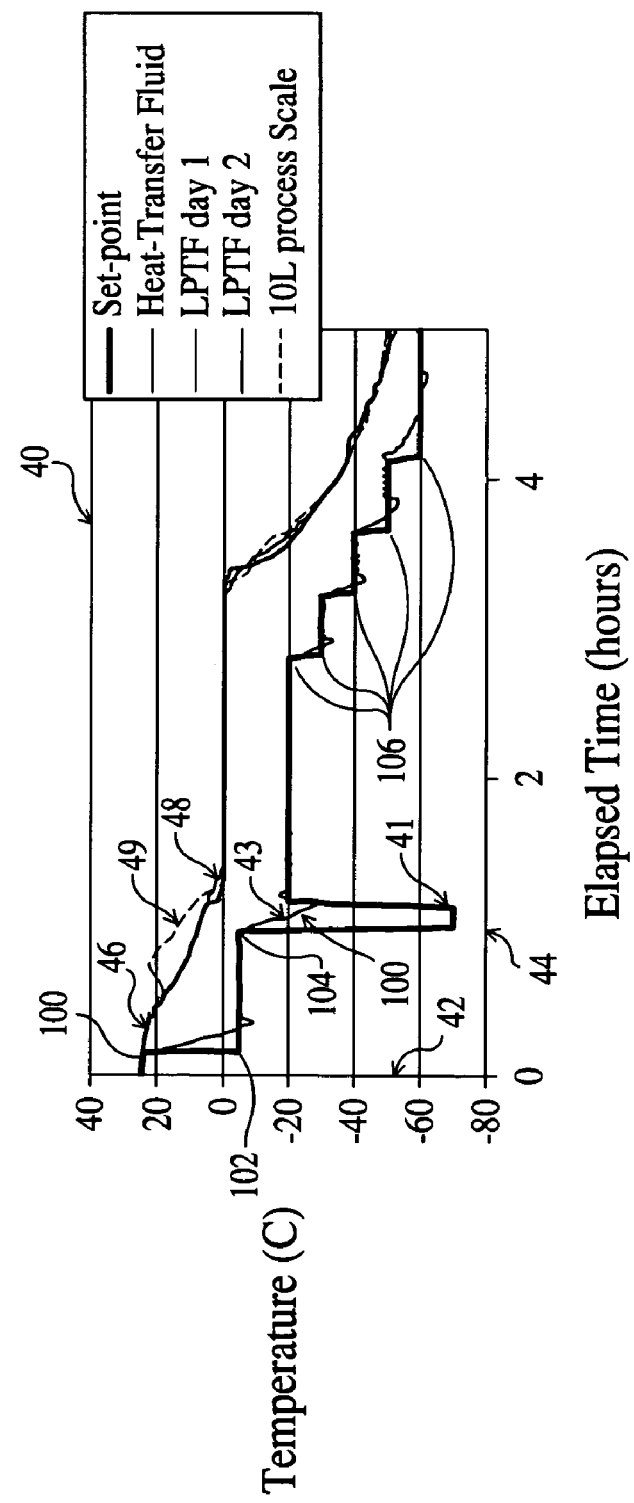
FIG. 4 is a freezing profile for a small-scale process and a large-scale process for the same specimen type.

FIG. 4 is a graph 40 showing an example of a freezing profile with temperature on the Y axis 42 versus time in hours on the X axis 44 for a sample-size (in this example, 30 mL) container on two different dates processed in the system of FIG. 1, compared to a large-scale process (10 L sample). The results for both sizes are for the same specimen type. Line 46 in the graph shows the results for the LPTF (Last Point to Freeze) on the second day, while line 48 shows the LPTF results for the first day of testing with the system of FIG. 1. In the present example, the LPTF is in the upper central portion of the container. Also shown in the graph for comparison are the results 49 for a large-scale process for a 10 liter specimen of the same bioproduct. Finally, graph 40 also shows the temperature setpoint 41 and temperature of the heat-transfer fluid supply 43, which can optionally be changed during the process. Also, the temperature of the fluid supply and outlet are preferably monitored and used in the control scheme.

As shown graphically in the example of FIG. 4, a multi-step temperature setpoint 41 program has been implemented to deliver a controlled temperature profile 43 for the heat-transfer fluid. The heat-transfer fluid temperature profile 43 used with the system of FIG. 1 is designed to mimic the freezing characteristics of a large-scale unit. This profile is carefully adjusted to take into account changes in chiller cooling dynamics and cooling capacity, as well as changes in overall heat exchange efficiency between large-scale and small-scale units.

In the example of FIG. 4, the setpoint temperature profile 41 comprises a short equilibration step 100 designed to smooth initial temperature differences. The next step in the setpoint profile is a cooling phase 102 designed to equilibrate the system to a low temperature value close to the phase change temperature. A steep decrease 104 of the heat-transfer fluid temperature is then generated for a short period of time, in order to promote ice nucleation at the tips of the container edges. During this transient period, the temperature of the container walls contacting the heat exchange elements drops quickly below the solidification temperature of the bioproduct (an aqueous solution), resulting in deliberate ice nucleation. The ice formed at these edges will then propagate through the container in the form of two opposite fronts (see FIG. 3), and the velocity of those fronts depends on the thermodynamic properties of the solidified mass and the heat removal performance of the system. A high control of the freezing front velocity is achieved by modulating the temperature of the heat-transfer fluid that circulates through the heat-exchange structure. The cooling of the fully solidified mass to the final desired storage temperature is then achieved at a rate representative of the performances of the large-scale unit. The rate of final cooling for the small-scale unit in this example is controlled by a multi-step adjustment 106 of the heat-transfer fluid temperature. Control of the heat-transfer fluid flow rate and/or cooling capacity of the heat removal system are examples of alternatives for controlling the rate of heat exchange in the small-scale unit.

Although not shown in FIG. 4, it will be understood that a similar approach could be applied to mimic at a small scale the thawing characteristic of the same bioproduct on a large scale.

Adjustment of the heat-transfer rate by whatever means permits a fine-tuning of the temperature conditions for specific bioproduct requirements (e.g. proteins, cells, viruses, cell fragments, cellular components), with the objective to maximize bioproduct stability. In particular, faster freezing rates can be programmed, if required, for improved product stability.

As shown in FIG. 4, the solidification process occurring in the small-scale controlled freezing unit is characterized by the absence of supercooling in the remaining liquid phase. Supercooling is often associated with detrimental effects for bioproduct stability. Supercooling may induce stress in bioproducts through cold denaturation and by introducing a large ice/liquid interface. Supercooling is often more pronounced in a small volume compared to a large-scale batch. Elimination or minimization of supercooling in the small-scale unit described here, is achieved by an intimate and localized contact between the heat-conducting structures and the edges of the bioproduct containers, and by a steep temperature gradient provided by the heat-transfer fluid at the onset of crystal nucleation. The shapes of the structures in contact with the container provide the conduction pattern, as well as the temperature gradient beneficial to the early ice nucleation in the container ends. More information regarding this point can be found in U.S. Pat. No. 6,337,205, issued on Jan. 8, 2002 to Richard Wisniewski, which is herein incorporated by reference in its entirety.

As shown graphically in FIG. 4, a system such as that in the present example with a sample size of bioproduct does indeed mimic the freezing characteristics of the same bioproduct on a large scale. Thus, entities engaged in the larger scale freezing of bioproducts can use the present invention to obtain representative information of the freezing behavior of the bioproduct before a costly miscalculation or improper assumption is made.

Figure 5:
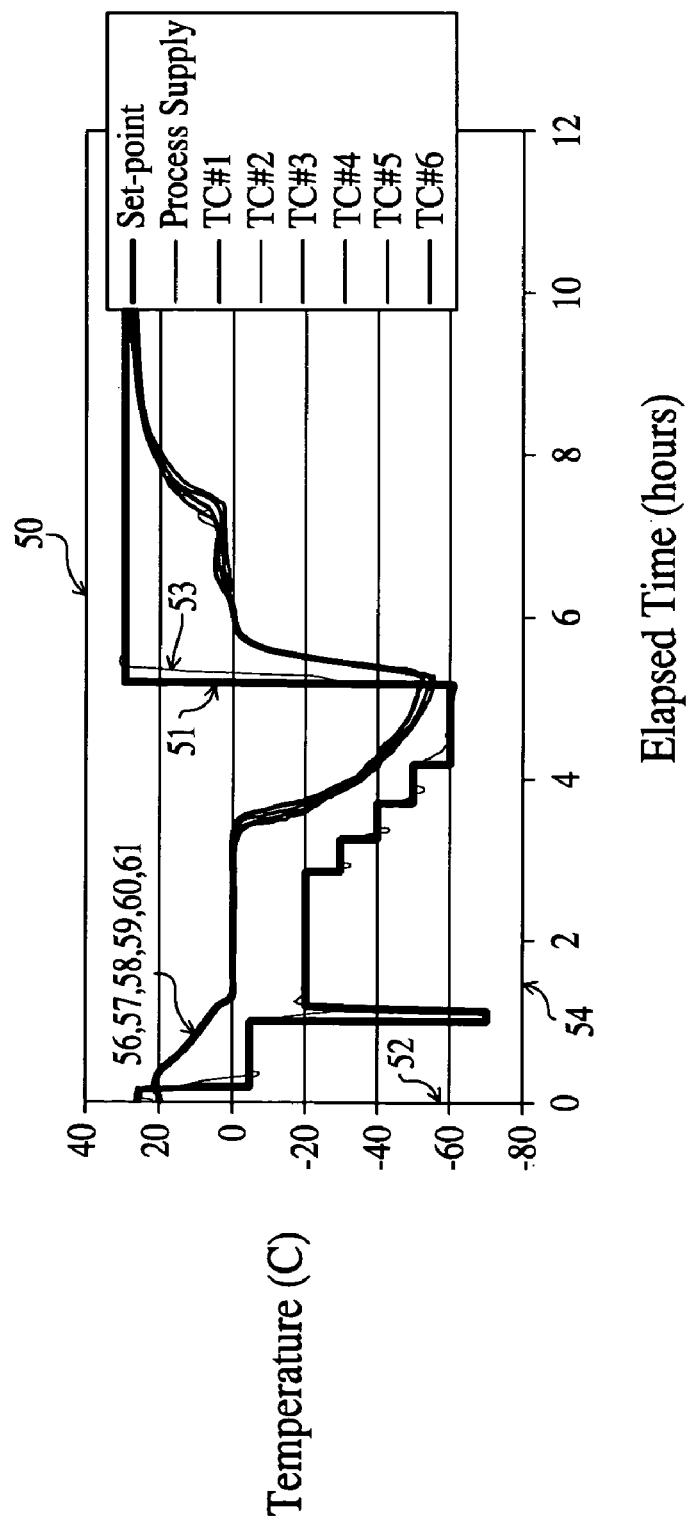
FIG. 5 is a freezing and thawing profile for another small quantity of specimen distributed in multiple containers.

FIG. 5 is a graph 50 showing an example of a freezing and thawing profile with temperature on the Y axis 52 versus time in hours on the X axis 54 for six small-size specimens, in this example 30 mL each, processed in parallel in the system of FIG. 1. Lines 56–61 show the freezing and thawing processing steps as represented by the temperature profiles in the upper central portion of the containers (in this example, bags). Also shown in graph 50 are the temperature setpoint profile 51 and the temperature profile of the heat-transfer fluid supply 53. As shown in FIG. 5, the initial liquid cooling is followed by the temperature plateau when the liquid phase in the center remains close to zero degrees Celsius and the side of the container freezes. After the freezing fronts reach the center and the whole product volume is frozen, the frozen product cools down to the prescribed temperature level. During thawing, the temperature of the heat transfer agent 53 is increased and the center point temperature increases, while the edges of the container are already thawed and the liquid there stays near zero degrees Celsius. The thawing can be conducted in a stationary state, or with movement of the freezing/thawing driving device, container and container-holding assembly to enhance the thawing process. Further details regarding thawing can be found in U.S. patent application Ser. No. 09/579,846, filed on May 26, 2000, and entitled "Cryopreservation Bag Assembly Structure," which is herein incorporated by reference in its entirety.

As shown graphically in FIG. 5, no significant difference in cooling, freezing or thawing is observed from container to container. In addition, no supercooooling can be detected prior to the phase change process. The system of the present invention provides a good uniformity and reproducibility of the thermal treatment, minimizing risks of deviation and potential risks of product degradation and/or loss. FIGS. 4 and 5 also show that complex freezing and thawing patterns can be achieved with the present invention. Note the example stepwise changes that are possible in the setpoint and coolant temperatures. Of course, other temperature profiles are also possible to obtain with the system. Such complex patterns allow for use with a wide variety of bioproducts.

Figure 6:
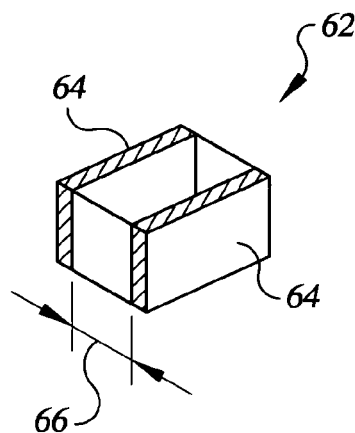
FIG. 6 depicts another example of a freezing and thawing unit with freezing/thawing driving devices in accordance the present invention.

FIG. 6 depicts another example of a freezing and thawing unit 62 with freezing/thawing driving devices 64, in accordance with the present invention. The freezing/thawing driving devices are, for example, the same type as in FIG. 1. Structural flexibility of unit 62, if desired, can be provided through the choice of materials, for example, plastic of varying strengths and compositions, depending on the application, could be used. As in the first example, when used for testing, a useable width 66 of the freezing and thawing unit is preferably the same as that which would be used for a specimen in the corresponding large-scale bioproduct freezing operation.

Figure 7:
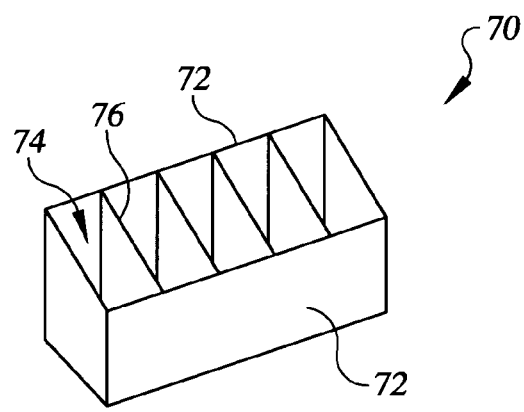
FIG. 7 depicts an example of a freezing and thawing unit with cells for bioproduct samples.

FIG. 7 depicts another example of a freezing and thawing unit 70, in accordance with the present invention. As with the example of FIG. 6, some mechanism for heat exchange (not shown) couplable to sides 72 is used to effect freezing and/or thawing. In addition, the freezing and thawing unit is broken up into cells (e.g., cell 74) for accepting bioproduct specimens. The specimens may be in their own container, as in the example of FIG. 3, but could instead be placed directly in the cells. In that regard, the cells are optionally liquid-tight with respect to each other to avoid a specimen from one cell contaminating another. In one example, dividers 76 are used to create the cells, and are made of, for example, the same material as the freezing and thawing unit. The dividers could be permanent or they could be removable inserts slid into slots in the sides, for example. The dividers can be selectively used to create cells of a desired size. Cells might also be left selectively empty.

Figure 8:
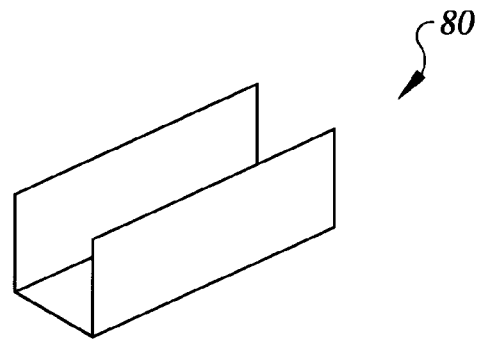
FIG. 8 depicts an optional heat-conductive cladding for use with the freezing and thawing unit of FIG. 7.

FIG. 8 depicts an optional heat-conductive cladding 80 that can be placed around the outside of the freezing and thawing units of FIG. 6 or 7 to improve heat transfer. The cladding could be made of various heat-conductive materials, for example, metal. One example of a heat-conductive metal that could be used is stainless steel.

Figure 9:
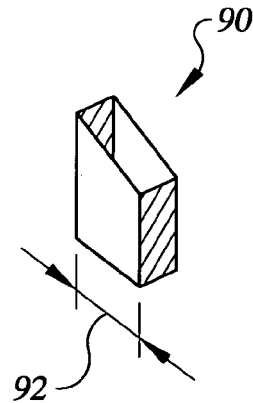
FIG. 9 depicts a cassette for holding bioproduct samples prior to insertion into a freezing and thawing unit.

FIG. 9 depicts a rectangular cassette 90 for holding a bioproduct specimen in the freezing and thawing unit of either FIG. 6 or FIG. 7. Such cassettes could be used in conjunction with the dividers described above, or could be used instead of the dividers. Such cassettes can be made of the same material as the freezing and thawing unit or a different material, for example, stainless steel, titanium and its alloys, aluminum and its alloys, polymers and composites, etc., and can be of different sizes to suit the application. In one example, the width 92 of the cassette corresponds to a cross-sectional thickness for a container used in a corresponding large-scale process, similar to the bag in FIG. 3.

Figure 10:
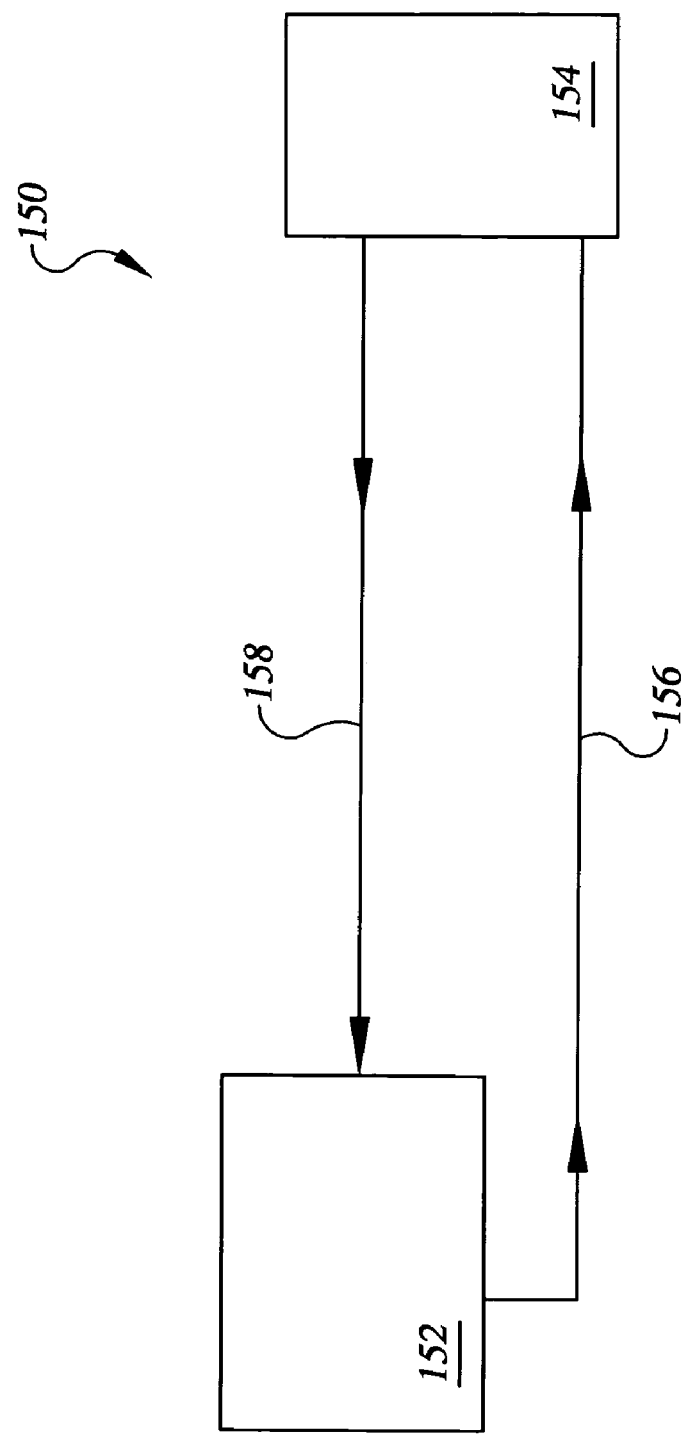
FIG. 10 is a block diagram of one example of a freezing and thawing system in accordance with the present invention.

FIG. 10 is a block diagram of one example of a freezing and thawing system 150 in accordance with the present invention. The system comprises a freezing and thawing unit 152 using a liquid heat-exchange medium, for example, freezing and thawing unit 10 in FIG. 1. A control unit 154 controls the temperature and flow rate of the liquid heat-exchange medium. One example of such a control unit is the CRYOPILOT offered by Integrated Biosystems, Inc., in Napa, Calif. System 150 is closed, such that the heat-exchange medium circulates continuously, traveling from the freezing and thawing unit to the control unit over line 156, and from the control unit to the freezing and thawing unit over line 158. The control unit can operate, in one example, in an automated fashion via computer control, or, in another example, through the use of manual controls.

While several aspects of the present invention have been described and depicted herein, alternative aspects may be effected by those skilled in the art to accomplish the same objectives. Accordingly, it is intended to cover all such alternative aspects as fall within the true spirit and scope of the invention.

The invention claimed is:

1. Apparatus for at least one of freezing and thawing at least one bioproduct, comprising:
    a unit for at least one of freezing and thawing at least one bioproduct on a small scale, the unit comprising at least two opposite surfaces for accepting a bioproduct container for the unit when the bioproduct container is present;
    wherein at least one of the at least two opposite surfaces is configured to be coupled to at least one driving device for at least one of freezing and thawing, wherein at least one of (a) a spacing of the at least two opposite surfaces and (b) a width of the bioproduct container for the unit, is sized to simulate a depth of a larger bioproduct container for a larger-scale unit taken between freezing surfaces of the larger bioproduct container, and wherein information about the at least one bioproduct at the large scale is deducible from actual information obtained for the at least one bioproduct at the small scale.

2. The apparatus of claim 1, further comprising at least one driving device for at least one of freezing and thawing, wherein the at least one driving device is coupleable to the at least one of the at least two opposite surfaces.

3. The apparatus of claim 2, wherein the at least one driving device comprises at least one conduit for a heat-transfer fluid.

4. The apparatus of claim 3, wherein the at least one conduit comprises a winding conduit.

5. The apparatus of claim 1, further comprising at least two clamping arrays coupled to the unit for holding a plurality of bioproduct containers.

6. The apparatus of claim 5, wherein the at least two clamping arrays are coupled to the at least two opposite surfaces of the unit.

7. The apparatus of claim 1, further comprising at least one container situatable within the unit for containing the at least one bioproduct.

8. The apparatus of claim 1, wherein the unit comprises a plurality of cells for holding the at least one bioproduct.

9. The apparatus of claim 8, further comprising at least one divider for creating the plurality of cells.

10. The apparatus of claim 9, wherein at least one of the at least one divider is removable without dismantling the unit.

11. The apparatus of claim 1, further comprising a heat-conductive cladding for the unit.

12. The apparatus of claim 11, wherein the heat-conductive cladding comprises a metal.

13. A system for performing at least one of freezing and thawing of at least one bioproduct on a small scale, comprising:
  a unit for at least one of freezing and thawing at least one bioproduct on a small scale, the unit comprising at least two opposite surfaces for accepting a bioproduct container for the unit when the bioproduct container is present;
  at least one driving device for at least one of freezing and thawing coupleable to at least one of the at least two opposite surfaces, wherein at least one of the at least two opposite surfaces is configured to be coupled to the at least one driving device; and
  at least one container for containing at least one bioproduct specimen within the unit;
  wherein at least one of (a) a spacing of the at least two opposite surfaces and (b) a width of the at least one container, is sized to simulate a depth of a larger bioproduct container for a larger-scale unit taken between freezing surfaces of the larger bioproduct container, and wherein information about the at least one bioproduct at the large scale is deducible from actual information obtained for the at least one bioproduct at the small scale.

14. The system of claim 13, wherein the at least one driving device comprises at least one conduit for a heat-transfer fluid.

15. The system of claim 14, wherein the at least one conduit comprises a winding conduit.

16. The system of claim 13, further comprising at least two clamping arrays coupled to the unit for holding a plurality of bioproduct containers.

17. The system of claim 16, wherein the at least two clamping arrays are coupled to the at least two opposite surfaces of the unit.

18. The system of claim 13, wherein the at least one container is integral with the unit.

19. The system of claim 18, wherein the at least one container comprises a plurality of cells for holding the at least one bioproduct.

20. The system of claim 19, further comprising at least one divider for creating the plurality of cells.

21. The system of claim 20, wherein at least one of the at least one divider is removable.

22. The system of claim 13, wherein the at least one container is separate from and situatable within the unit.

23. The system of claim 13, further comprising a heat-conductive cladding for the unit.

24. The system of claim 23, wherein the heat-conductive cladding comprises a metal.

25. A method of performing at least one of freezing and thawing of at least one bioproduct on a small scale, comprising:
  providing a unit for at least one of freezing and thawing at least one bioproduct, the unit comprising at least two opposite surfaces for accepting a bioproduct container for the unit when the bioproduct container is present;
  coupling at least one of the at least two opposite surfaces to at least one driving device for at least one of freezing and thawing; and
  performing at least one of freezing and thawing on the at least one bioproduct, wherein the bioproduct is situated within the unit;
  wherein at least one of (a) a spacing of the at least two opposite surfaces and (b) a dimension of the bioproduct container for the unit, is sized to simulate a slice of a larger bioproduct container for a larger-scale unit taken between freezing surfaces of the larger bioproduct container, wherein the dimension is one of length, width and depth; and
  deducing information about the at least one bioproduct at the large scale from actual information obtained for the at least one bioproduct at the small scale.

26. The method of claim 25, further comprising situating the at least one bioproduct within the unit.

27. The method of claim 26, wherein the bioproduct is situated within a container, and wherein the situating comprises situating the container within the unit.

28. The method of claim 25, wherein the unit comprises a plurality of cells for accepting the at least one bioproduct, the method further comprising situating the at least one bioproduct within at least one of the plurality of cells.

29. The method of claim 25, wherein the performing comprises controlling a rate of heat exchange between the at least one driving device and the at least one bioproduct.

30. The method of claim 25, further comprising coupling at least one heat-conductive cladding to the unit.

31. The apparatus of claim 1, wherein the bioproduct container for the unit comprises a first bag, and wherein the bioproduct container for the larger-scale unit comprises a second bag larger than the first bag.

32. The system of claim 13, wherein the bioproduct container for the unit comprises a first bag, and wherein the bioproduct container for the larger-scale unit comprises a second bag larger than the first bag.

33. The method of claim 25, wherein the bioproduct container for the unit comprises a first bag, and wherein the bioproduct container for the larger-scale unit comprises a second bag larger than the first bag.

34. A method of making apparatus for at least one of freezing and thawing at least one bioproduct on a small scale, the method comprising:
   providing a unit for at least one of freezing and thawing at least one bioproduct on a small scale, the unit comprising at least two opposite surfaces for accepting a bioproduct container for the unit when the bioproduct container is present; and
   spacing the at least two opposite surfaces to proportionally correspond to a slice of a larger bioproduct container for a larger-scale unit taken between freezing surfaces of the larger bioproduct container.

35. The method of claim 34, further comprising coupling at least one driving device for at least one of freezing and thawing to the at least one of the at least two opposite surfaces.

36. The method of claim 34, further comprising coupling at least two clamping arrays to the unit for holding a plurality of bioproduct containers.

37. The method of claim 36, wherein the coupling comprises coupling the at least two clamping arrays to the at least two opposite surfaces.

38. The method of claim 34, further comprising coupling a heat-conductive cladding to the unit.

39. A method of making a system for at least one of freezing and thawing at least one bioproduct on a small scale, the method comprising:
   providing a unit for at least one of freezing and thawing at least one bioproduct on a small scale, the unit comprising at least two opposite surfaces for accepting a bioproduct container for the unit when the bioproduct container is present;
   providing at least one container for containing at least one bioproduct specimen within the unit; and
   sizing a dimension of the at least one container to proportionally correspond to a slice of a larger bioproduct container for a larger-scale unit taken between freezing surfaces of the larger bioproduct container.

40. The method of claim 39, further comprising coupling at least one driving device for at least one of freezing and thawing to the at least one of the at least two opposite surfaces.

41. The method of claim 39, further comprising coupling at least two clamping arrays to the unit for holding a plurality of bioproduct containers.

42. The method of claim 41, wherein the coupling comprises coupling the at least two clamping arrays to the at least two opposite surfaces.

43. The method of claim 39, further comprising coupling a heat-conductive cladding to the unit.

44. The method of claim 39, wherein providing the at least one container comprises providing at least one container integral with the unit.

45. The method of claim 44, wherein providing the at least one container integral with the unit comprises providing at least one container with a plurality of cells for holding the at least one bioproduct.

46. The method of claim 45, further comprising providing at least one divider for creating the plurality of cells.

47. The method of claim 46, wherein providing the at least one divider comprises providing at least one removable divider.

* * * * *